United States Patent
Kwok et al.

(10) Patent No.: US 11,083,864 B2
(45) Date of Patent: Aug. 10, 2021

(54) CONNECTOR SYSTEM FOR AN APPARATUS THAT DELIVERS BREATHABLE GAS TO A PATIENT

(71) Applicant: ResMed Pty Ltd, Bella Vista (AU)

(72) Inventors: Philip Rodney Kwok, Sydney (AU); Karthikeyan Selvarajan, Sydney (AU); James Morrison, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 1251 days.

(21) Appl. No.: 14/926,633

(22) Filed: Oct. 29, 2015

(65) Prior Publication Data
US 2016/0051788 A1 Feb. 25, 2016

Related U.S. Application Data

(62) Division of application No. 11/920,756, filed as application No. PCT/AU2006/000679 on May 22, 2006, now Pat. No. 9,211,398.
(Continued)

(51) Int. Cl.
*A61M 16/08* (2006.01)
*A61M 16/06* (2006.01)
(Continued)

(52) U.S. Cl.
CPC .... *A61M 16/0875* (2013.01); *A61M 16/0009* (2014.02); *A61M 16/0057* (2013.01);
(Continued)

(58) Field of Classification Search
CPC .......... A61M 16/0875; A61M 16/0816; A61M 16/0841; A61M 39/10; A61M 39/1055
See application file for complete search history.

(56) References Cited

U.S. PATENT DOCUMENTS 1,033,554 A * 7/1912 Dickinson ........... F16L 37/1215
285/34
2,340,926 A 2/1944 Bradley
(Continued)

FOREIGN PATENT DOCUMENTS

DE 199 54 724 A1 6/2001
WO 03/026721 A2 4/2003

OTHER PUBLICATIONS

Written Opinion of the International Searching Authority for PCT/AU2006/000679, dated Aug. 19, 2006.
(Continued)

*Primary Examiner* — LaToya M Louis
(74) *Attorney, Agent, or Firm* — Nixon & Vanderhye P.C.

(57) ABSTRACT

A connector system for use with an apparatus that delivers a supply of pressurized breathable air to a patient includes an air delivery conduit including an auxiliary conduit. The air delivery conduit and auxiliary conduit have a first end and a second end. A connector is provided to at least one of the first and second ends. The connector includes an inner tubular wall and an outer tubular wall surrounding the inner tubular wall and being concentric with the inner tubular wall. The inner and outer tubular walls define first and second passages that are isolated from one another. One of the first and second passages is configured to communicate with the air delivery conduit and the other of the first and second passages is configured to communicate with the auxiliary conduit.

42 Claims, 13 Drawing Sheets

Related U.S. Application Data

(60) Provisional application No. 60/775,335, filed on Feb. 22, 2006, provisional application No. 60/683,338, filed on May 23, 2005.

(51) Int. Cl.
  *A61M 16/00* (2006.01)
  *A61M 39/08* (2006.01)
  *A61M 39/10* (2006.01)
  A61M 16/14 (2006.01)
  A61M 16/16 (2006.01)
  A61M 16/20 (2006.01)

(52) U.S. Cl.
  CPC ........ *A61M 16/06* (2013.01); *A61M 16/0638* (2014.02); *A61M 16/085* (2014.02); *A61M 16/0816* (2013.01); *A61M 16/0858* (2014.02); *A61M 39/08* (2013.01); *A61M 39/10* (2013.01); A61M 16/0605 (2014.02); A61M 16/14 (2013.01); A61M 16/16 (2013.01); A61M 16/208 (2013.01); A61M 2016/0027 (2013.01); A61M 2202/0208 (2013.01); A61M 2205/0222 (2013.01); A61M 2205/10 (2013.01); A61M 2205/3334 (2013.01); A61M 2205/3375 (2013.01); A61M 2205/42 (2013.01)

(56) References Cited

U.S. PATENT DOCUMENTS

| | | | | |
|---|---|---|---|---|
| 3,372,715 | A * | 3/1968 | Ashton | B67D 7/002 137/615 |
| 3,490,496 | A | 1/1970 | Stearns | |
| 3,777,502 | A | 12/1973 | Michie | |
| 4,109,944 | A * | 8/1978 | Curtin | F16L 47/26 285/373 |
| 4,214,358 | A * | 7/1980 | Clerc | B21D 39/04 285/148.11 |
| 4,462,397 | A | 7/1984 | Suzuki | |
| 4,676,241 | A * | 6/1987 | Webb | A61M 16/08 128/207.14 |
| 4,794,921 | A | 1/1989 | Lindkvist | |
| 4,815,452 | A | 3/1989 | Hayek | |
| 5,284,160 | A | 2/1994 | Dryden | |
| 5,921,591 | A * | 7/1999 | Argent | E21B 17/0426 228/135 |
| 6,378,517 | B1 | 4/2002 | Steen | |
| 6,484,724 | B1 | 11/2002 | Sloan | |
| 6,536,428 | B1 | 3/2003 | Smith et al. | |
| 6,564,831 | B1 * | 5/2003 | Sanoner | F16L 9/19 138/115 |
| 6,571,794 | B1 | 6/2003 | Hansen | |
| 6,662,802 | B2 | 12/2003 | Smith et al. | |
| 6,874,500 | B2 | 4/2005 | Fukunaga et al. | |
| 7,040,018 | B2 * | 5/2006 | Lohbeck | E21B 17/042 29/890.144 |
| 7,137,388 | B2 | 11/2006 | Virr et al. | |
| 7,874,292 | B2 | 1/2011 | Smith et al. | |
| 9,211,398 | B2 * | 12/2015 | Kwok | A61M 16/0816 |
| 2002/0148464 | A1 | 10/2002 | Hoenig | |
| 2004/0112384 | A1 | 6/2004 | Lithgow et al. | |
| 2004/0123914 | A1 | 7/2004 | Chih | |
| 2004/0130150 | A1 * | 7/2004 | Stark | F16L 27/0808 285/272 |
| 2005/0150505 | A1 * | 7/2005 | Burrow | A61M 16/0816 128/204.18 |

OTHER PUBLICATIONS

International Search Report for PCT/AU2006/000679, dated Aug. 19, 2006.
U.S. Appl. No. 60/706,430, filed Aug. 8, 2005 (p. 7 of specification).
Utility U.S. Appl. No. 10/467,304, filed Feb. 14, 2002 (p. 8 of specification, U.S. Pat. No. 7,137,388).
Utility U.S. Appl. No. 10/655,603, filed Sep. 5, 2003 (p. 10 of specification, published as U.S. Publication No. 2004/0112384).
International Preliminary Report on Patentability for PCT/AU2006/000679, dated Nov. 23, 2007 (6 pgs.).

* cited by examiner

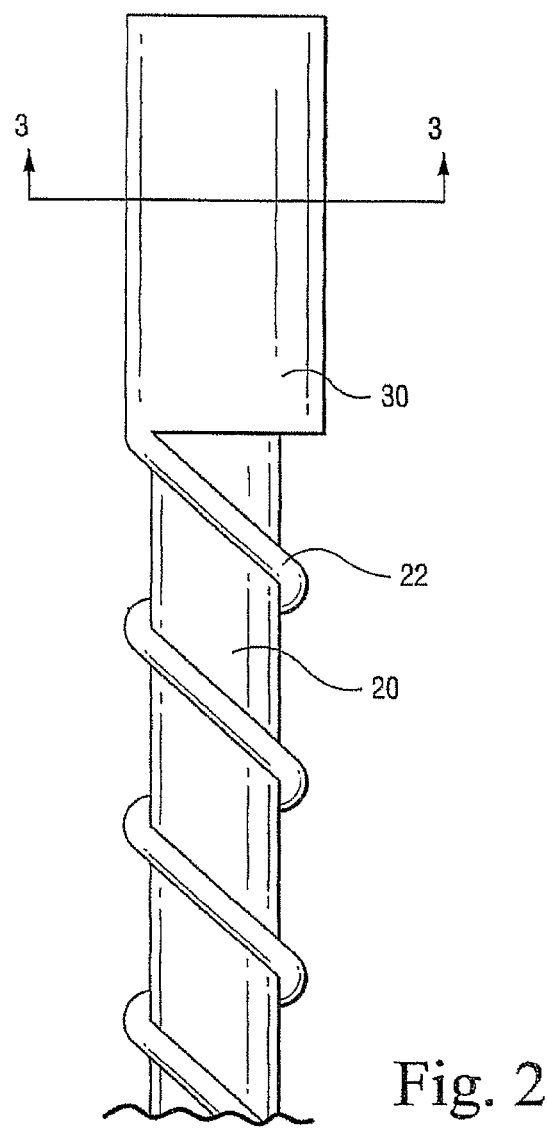
Fig. 2
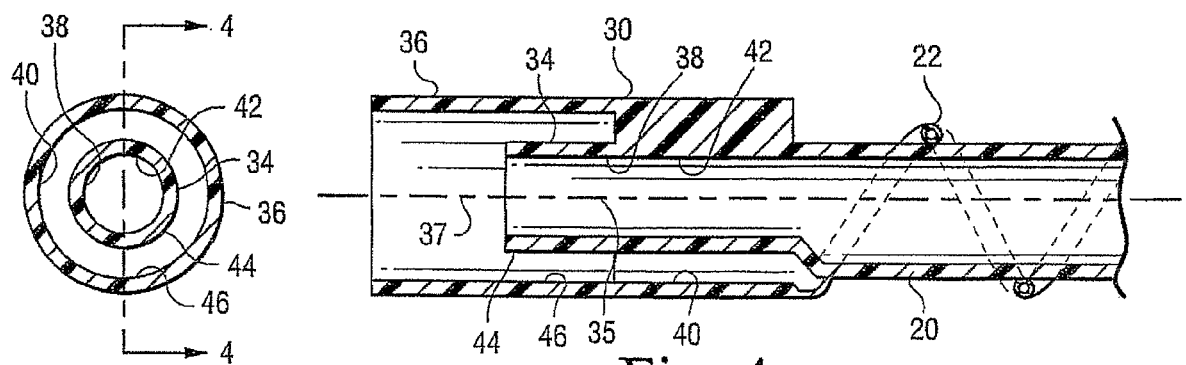
Fig. 3
Fig. 4

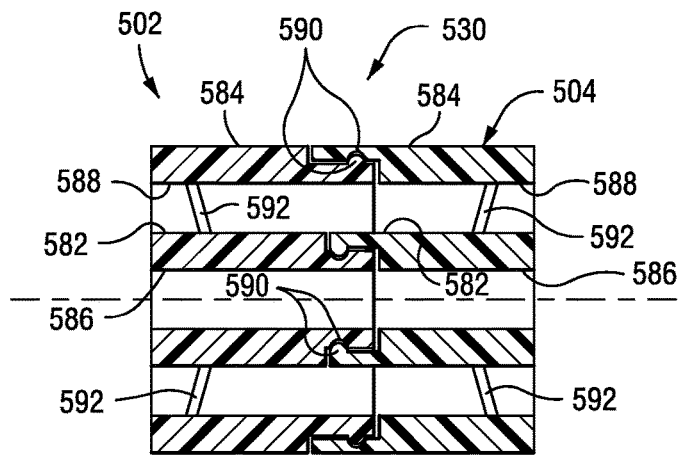
Fig. 14
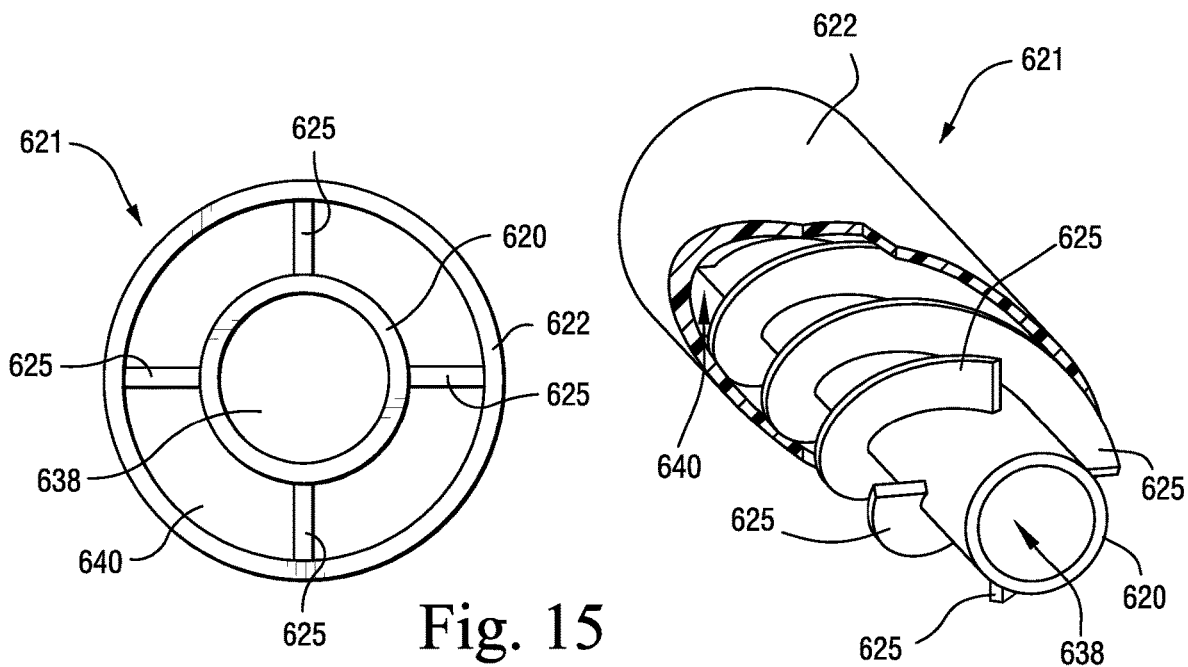
Fig. 15
Fig. 15A
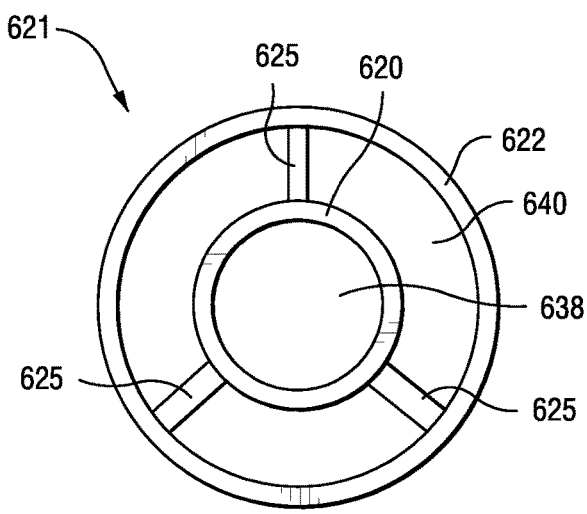
Fig. 16

CONNECTOR SYSTEM FOR AN APPARATUS THAT DELIVERS BREATHABLE GAS TO A PATIENT

CROSS-REFERENCE TO RELATED APPLICATIONS

This application is a divisional of U.S. application Ser. No. 11/920,756, filed Nov. 20, 2007, which is a U.S. national phase of International Application No. PCT/AU2006/000679, filed May 22, 2006, which designated the U.S. and claims priority to U.S. Provisional Application Nos. 60/683,338, filed May 23, 2005, and 60/775,335, filed Feb. 22, 2006, each of which is incorporated herein by reference in its entirety.

FIELD OF THE INVENTION

The present invention relates to an apparatus that delivers breathable gas to a patient.

BACKGROUND OF THE INVENTION

Apparatus to deliver breathable gas to a patient typically include a flow generator, an air delivery conduit, and a patient interface, wherein the air delivery conduit delivers pressurized air from the flow generator to the patient interface in contact with the patient's face. Throughout a range of air delivery systems, from both simple CPAP systems to more complex non-invasive positive pressure ventilation (NIPPV), there is frequently a need for communication between the patient interface and the flow generator, other than through the air delivery conduit. This communication thus requires a second conduit routed from the flow generator to the patient interface.

One example of this requirement is the measure of pressure. The pressure delivered to the entrance of the patient's airways is generally estimated by measuring the pressure at the flow generator and applying a correction factor in accordance with the known characteristics of the relevant conduit and patient interface. The pressure delivered to the entrance of the patient's airways can also be measured directly in the patient interface. In this case, a pressure transducer may be mounted on or near the patient interface and in communication with the interior of the patient interface by way of a port or linking sensing tube. Alternatively, the sensing tube is connected between an appropriate port on the patient interface and a pressure transducer located remotely from the patient interface such as in the flow generator housing. An example of this type of system is the SULLIVAN® Constant CPAP manufactured by ResMed Ltd, Australia, which uses 3 mm-diameter tubing.

A further example of where a separate communication tube may be required is where sampling of the gas is required, for oxygen or carbon dioxide monitoring for example. Alternatively, the supply of oxygen or any drug delivery system may require a separate tube communication system between the flow generator or any remote location within the hose system and the patient interface.

When these pressure sensing or air delivery tubes are a separate component to the main air delivery conduit, the sensing tube can become tangled or occluded if bent. The sensing tubes above are also cumbersome to handle and assemble by the user. In an attempt to address some of these disadvantages, systems have secured the sensing tube and the gas conduit together with clips or the like to form a tubing assembly. However this approach requires additional components and can be cumbersome and difficult to assemble. An alternative approach is to incorporate the additional communication system (e.g., sensing tube) with the air delivery conduit such as the system described within DE19954724 to Bernd. One embodiment shows a spiral tube incorporated around the exterior of the air delivery conduit. A range of respiratory conduits are shown within WO 03/026721 A2 to Schein, that incorporate tubes within the respiratory conduit.

Any of the systems described above that connect an additional communication system or auxiliary tube between the patient interface and the flow generator or other device at a distance along the air delivery conduit requires a connection system between the components. This connection may occur between the patient interface and the air delivery conduit, the air delivery conduit and the flow generator, or the air delivery conduit and intermediate components such as humidifiers. This connection mechanism should ideally be easy to assemble, non-directional, secure, lightweight and easy to clean.

An example of an existing connector system is shown in DE19954724, which may be used with MAP components such as the MAP MiniMax humidifier. As shown in FIG. 5 of DE19954724 (See FIG. 19 of the current application), one of the connections requires connection of a port incorporated within the cuff that requires alignment with the patient interface or connection device. As shown in FIG. 6 of DE 19954724 (See FIG. 20 of the current application), another one of the connections requires connection of an external tube with both the patient interface and a port on the air delivery conduit cuff. This solution requires dexterity by the patient in the correct assembly and alignment of the components.

SUMMARY OF THE INVENTION

One aspect of the present invention relates to a connector system that facilitates the assembly of an air delivery conduit incorporating an auxiliary conduit with a patient interface or other component of an apparatus that delivers breathable gas.

Another aspect of the invention relates to a connector system for use with an apparatus that delivers a supply of pressurized breathable air to a patient. The connector system includes an air delivery conduit including an auxiliary conduit. The air delivery conduit and auxiliary conduit have a first end and a second end. A connector is provided to at least one of the first and second ends. The connector includes an inner tubular wall and an outer tubular wall surrounding the inner tubular wall and being concentric with the inner tubular wall. The inner and outer tubular walls define first and second passages that are isolated from one another. One of the first and second passages is configured to communicate with the air delivery conduit and the other of the first and second passages is configured to communicate with the auxiliary conduit.

Another aspect of the invention relates to a connector system for use with an apparatus that delivers a supply of pressurized breathable air to a patient. The apparatus includes at least two components. The connector system includes an air delivery conduit including an auxiliary conduit. The air delivery conduit and auxiliary conduit have a first end provided to one of the components and a second end provided to another of the components. A connector is provided to at least one of the first and second ends. The connector includes an inner tubular wall and an outer tubular wall surrounding the inner tubular wall. The inner and outer tubular walls define first and second passages that are isolated from one another. One of the first and second passages are configured to communicate with the air delivery conduit and the other of the first and second passages are configured to communicate with the auxiliary conduit. The connector is attachable to at least one of the components in a plurality of orientations.

Yet another aspect of the invention relates to a dual air conduit for use with an apparatus that delivers a supply of pressurized breathable air to a patient. The dual air conduit includes an outer conduit, an inner conduit coaxially arranged within the outer conduit, and one or more support webs to separate the inner and outer conduits. The inner and outer conduits define first and second passages that are isolated from one another.

Yet another aspect of the invention relates to a low friction air delivery conduit for use with an apparatus that delivers a supply of pressurized breathable air to a patient. The low friction air delivery conduit includes a tubular wall having an internal diameter and one or more support webs that internally support the tubular wall. The one or more webs are arranged to extend across the internal diameter or a chord of the tubular wall. The tubular wall is structured such that at least an external surface is relatively smooth to provide relatively low friction properties.

Still another aspect of the invention relates to a swivel connector system having two or more concentric air passageways. In an embodiment, the system includes first and second connectors. The inner walls of the first connector are adapted to interlock with the inner walls of the second connector. The outer walls of the first connector are adapted to interlock with the outer walls of the second connector. In both cases, the interlocking may be achieved by virtue of a circumferential rib and groove arrangement, or other means.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 2 is a side view illustrating a connector system in accordance with an embodiment of the present invention;

FIG. 3 is a cross-sectional view through line 3-3 of FIG. 2;

FIG. 4 is a cross-sectional view through line 4-4 of FIG. 3;

FIGS. 9B-10 are perspective views illustrating a connector system according to still another embodiment of the present invention;

FIG. 14 is a cross-sectional view illustrating a connector system according to yet another embodiment of the present invention;

FIGS. 15-16 illustrate coaxial dual air conduits according to embodiments of the present invention;

DETAILED DESCRIPTION OF ILLUSTRATED EMBODIMENTS

FIGS. 1-5 illustrate a connector system 10 constructed according to an embodiment of the present invention. The connector system 10 is structured for use with an apparatus 12 that delivers a supply of pressurized breathable air to a patient for treatment, e.g., of Sleep Disordered Breathing (SDB) with CPAP or Non-Invasive Positive Pressure Ventilation (NIPPY).

Figure 1:
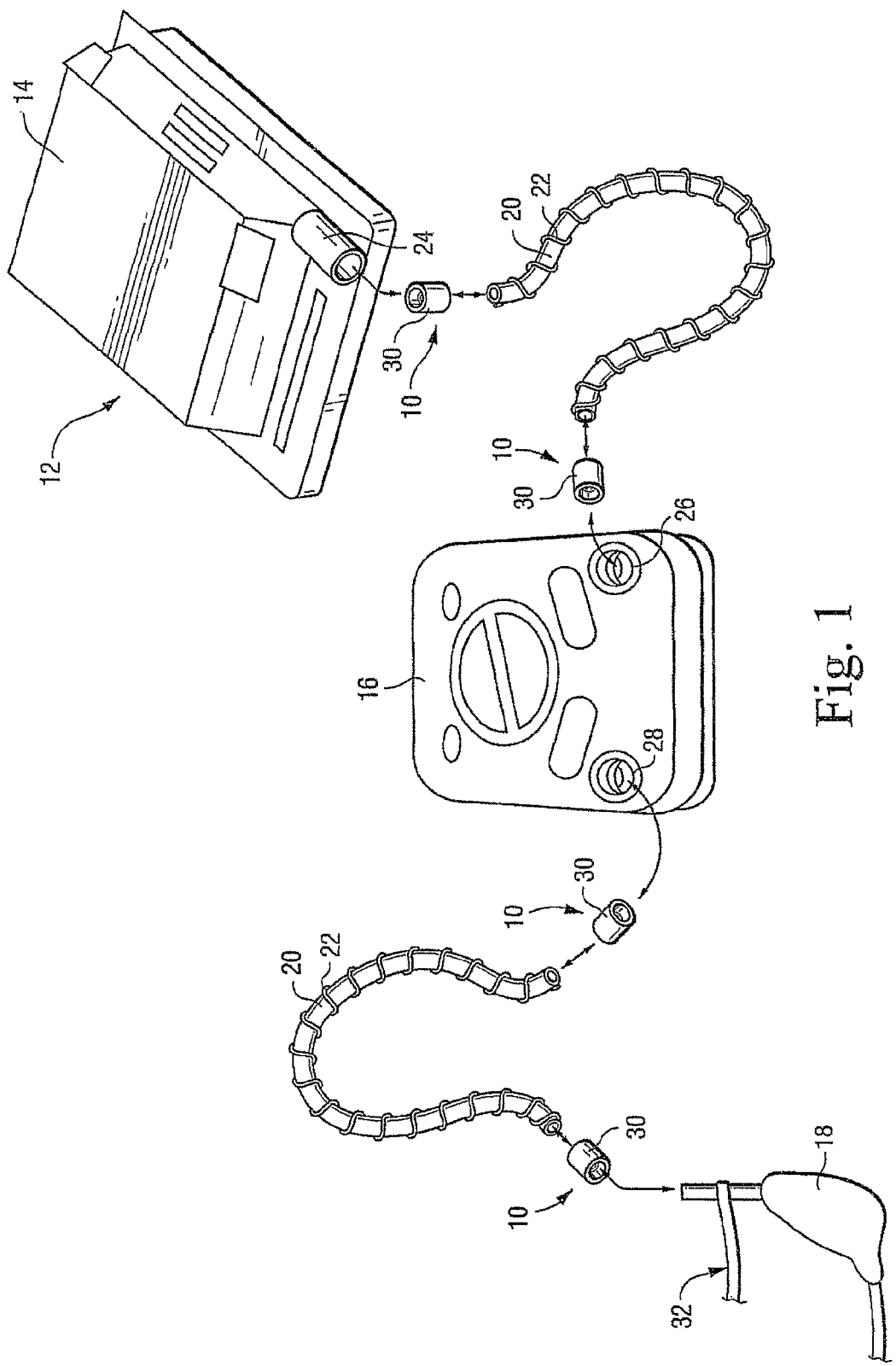
FIG. 1 is a perspective view of an apparatus that delivers breathable gas to a patient, the apparatus including a connector system constructed according to an embodiment of the present invention.

As best shown in FIG. 1, the apparatus 12 generally includes a flow generator 14, an optional humidifier 16, and a patient interface 18. An air delivery conduit 20 including an auxiliary conduit 22 is coupled between the flow generator 14 and the humidifier 16, and another air delivery conduit 20 including an auxiliary conduit 22 is coupled between the humidifier 16 and the patient interface 18. As discussed in greater detail below, each end of the air delivery conduits 20 including auxiliary conduits 22 includes a connector system 10 in the form of a dual cuff connector 30. The connector 30 is shown schematically in FIG. 1 and may be formed in one-piece with or separately from conduit 20 and/or conduit 22. The dual cuff connector 30 can, in one action and without concern as to the orientation of the cuff, connect both the air delivery conduit 20 and the auxiliary conduit 22 to respective components of the apparatus 12.

Flow Generator

The flow generator 14 is structured to provide a pressurized flow of air at an outlet 24. The supply of pressurized air is delivered to the humidifier 16 via the air delivery conduit 20 that includes one end coupled to the outlet 24 of the flow generator 14 and an opposite end coupled to the inlet 26 of the humidifier 16. The supply of pressurized air is exposed to a volume of liquid within the humidifier 16, and a supply of humidified pressurized air is provided at an outlet 28 of the humidifier 16. The supply of humidified pressurized air is delivered to the patient interface 18 via the air delivery conduit 20 that includes one end coupled to the outlet 28 of the humidifier 16 and an opposite end coupled to the patient interface 18.

Patient Interface

The patient interface 18 comfortably engages the patient's face and provides a seal. The patient interface 18 may have any suitable configuration as is known in the art, e.g., full-face mask, nasal mask, oro-nasal mask, mouth mask; nasal prongs, etc. Also, any suitable headgear arrangement 32 may be utilized to comfortably support the patient interface 18 in a desired position on the patient's face.

Air Delivery Conduit including Auxiliary Conduit

As noted above, each air delivery conduit 20 includes an auxiliary conduit 22 that allows communication between the components of the apparatus 12, other than through the air delivery conduit 20. For example, the auxiliary conduit 22 may provide supplemental air, pressure measurement, sound measurement, gas sampling, drug delivery, etc. In another embodiment, the auxiliary conduit 22 may be used as a vent to vent air from the patient interface. Moreover, a vacuum may be applied to the auxiliary conduit 22 to forcibly extract the vented air. An embodiment of this type of arrangement is provided in the U.S. Provisional Application No. 60/706,430, entitled "Ventless Mask CPAP System" and filed Aug. 8, 2005, incorporated herein by reference in its entirety.

As illustrated, the auxiliary conduit 22 is coiled around the air delivery conduit 20, e.g., helically wound. However, the auxiliary conduit 22 may be coupled to the air delivery conduit 20 in any other suitable manner. As shown in FIG. 1, opposing ends of the air delivery conduit 20 and auxiliary conduit 22 are coupled to a dual cuff connector 30, which couples the air delivery conduit 20 and auxiliary conduit 22 to the respective component of the apparatus 12. That is, the same dual cuff connector 30 may be used at all junctions of the conduits 20, 22 and the components of the apparatus 12.

The connector 30 is preferably made of a rubber-like material similar to that of the conduits 20, 22 for compatibility therewith. Alternatively, the connector 30 may be made of any other suitable material, e.g., plastic, polycarbonate, etc., that allows connection to the conduits 20, 22.

The components of the apparatus 12 would be adapted for use with the dual cuff connector 30. For example, the humidifier may be similar to the humidifier disclosed in U.S. patent application Ser. No. 10/467,304, filed Feb. 14, 2002, incorporated herein by reference in its entirety, with both the inlet and the outlet of the humidifier being adapted for use with the dual cuff connector 30. Embodiments of the dual cuff connector 30 connected to components of the apparatus 12 are discussed in greater detail below.

First Embodiment Dual Cuff Connector

As shown in FIGS. 2-5, the dual cuff connector 30 includes an inner tubular wall 34 and an outer tubular wall 36 that surrounds the inner tubular wall 34. The outer tubular wall 36 is concentric with the inner tubular wall 34. That is, the inner tubular wall has an axis 35 that is axially aligned with an axis 37 of the outer tubular wall. The inner and outer tubular walls 34; 36 define first and second passages 38, 40 that are isolated from one another. Specifically, the interior surface 42 of the inner tubular wall 34 defines the first passage 38 that is configured to communicate with the air delivery conduit 20. The exterior surface 44 of the inner tubular wall 34 and the interior surface 46 of the outer tubular wall 36 define the second passage 40 that is configured to communicate with the auxiliary conduit 22.

As illustrated, the first passage 38 has a generally cylindrical configuration, and the second passage 40 has a generally annular configuration. Moreover, the passages 38, 40 are concentric or axially aligned so that orientation of the connector 30 with respect to the associated component of the apparatus 12 does not matter. That is, the connector 30 may be connected to the associated component independent of the relative rotative position of the connector 30.

Figure 5:
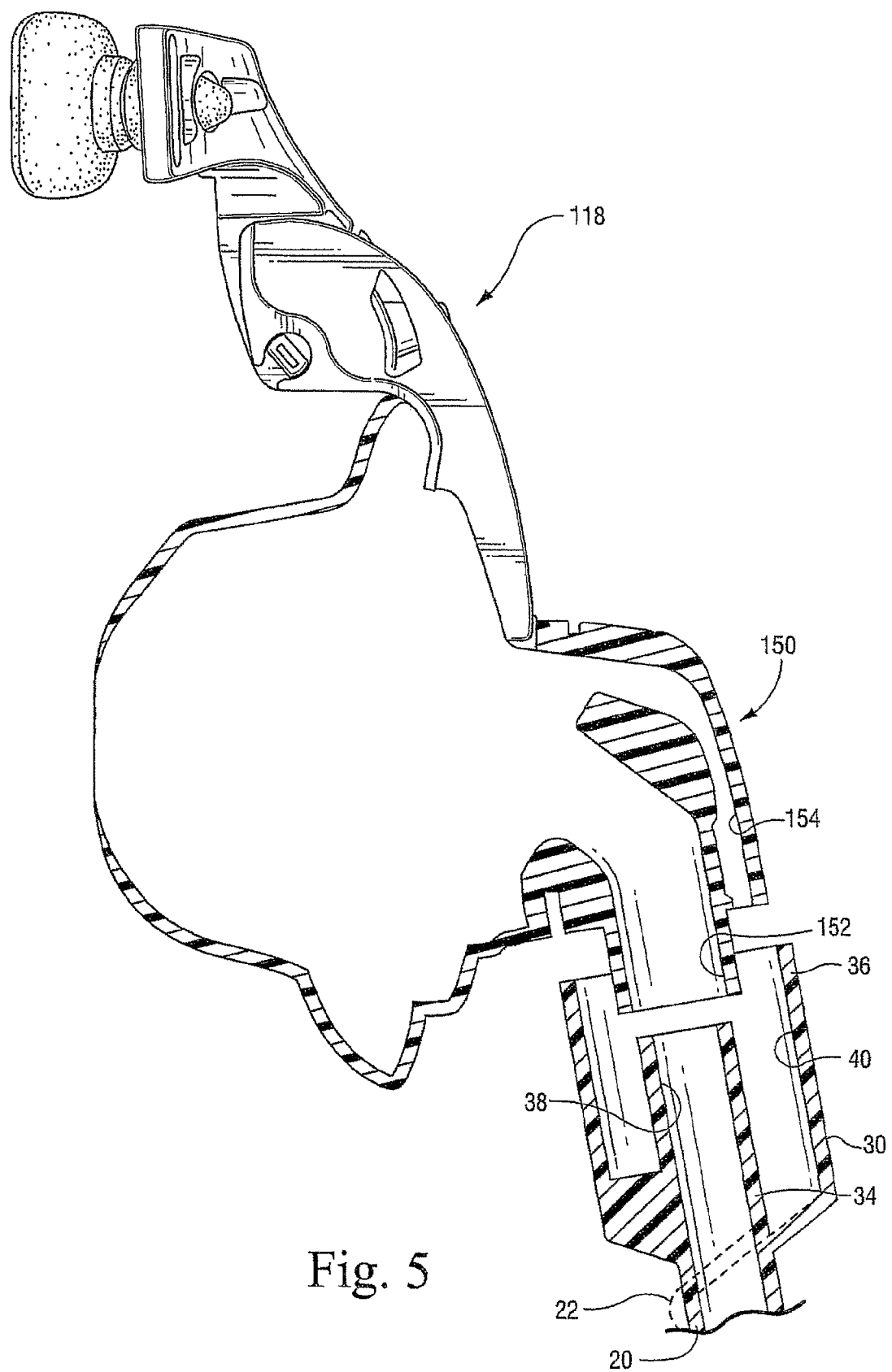
FIG. 5 is a partial cross-sectional view illustrating the connector system shown in FIG. 2 connected to a patient interface.

FIG. 5 illustrates the connector 30 being coupled to a patient interface 118. The patient interface 118 includes an elbow assembly 150 that provides a primary port 152 and a secondary port 154. As illustrated, the primary port 152 protrudes further outwardly than the secondary port 154. In the illustrated embodiment, the connector 30 is secured to the elbow assembly 150 with a friction fit. Specifically, the outer tubular wall 36 engages an exterior surface of the elbow assembly 150 with a friction fit, and the inner tubular wall 34 engages an interior surface of the primary port 152 with a friction fit. However, the connector 30 may be secured to the patient interface 118 in any other suitable manner. This arrangement provides a secure airtight seal, and allows the first passage 38 to communicate with the primary port 152 and the second passage 40 to communicate with the secondary port 154. Moreover, the connector 30 does not need to be aligned or oriented in any particular manner with the elbow assembly 150 to properly communicate the first and second passages 38, 40 with respective primary and secondary ports 152, 154.

In the illustrated embodiment of FIGS. 2-5, the outer tubular wall 36 is longer in the axial direction than the inner tubular wall 34. That is, the free end of the outer tubular wall 36 protrudes outwardly from the free end of the inner tubular wall 34. However, the inner and outer tubular walls 34, 36 may have any suitable arrangement.

Figure 5A:
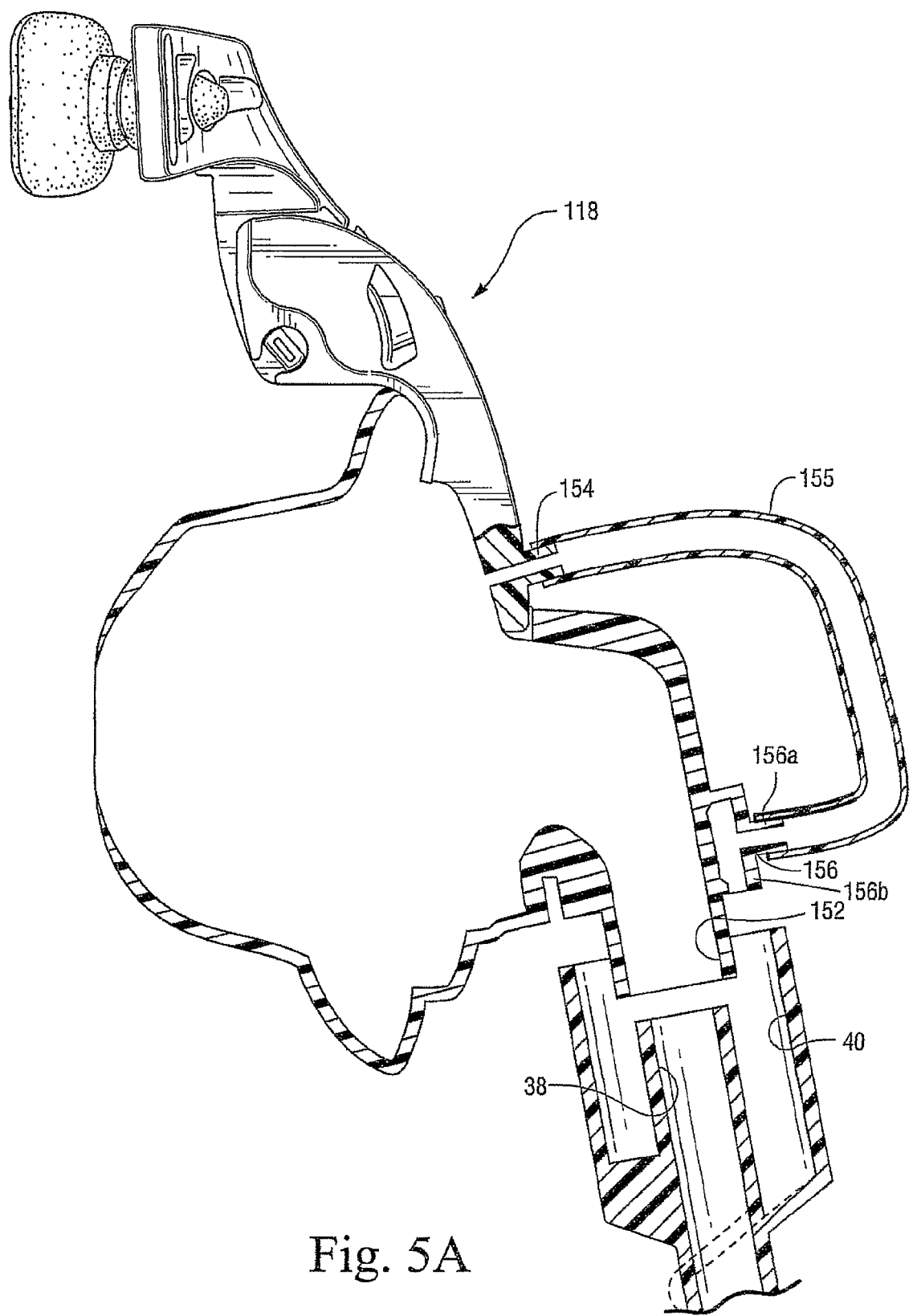
FIG. 5A is a cross-sectional view of another mask connector system example.

FIG. 5A illustrates yet another example of a dual cuff connector, which is another variation of the example shown in FIG. 5. In the example of FIG. 5A, patient interface 118 is provided with a secondary port 154 in the form of a generally cylindrical tube or spout. The patient interface 118 is also provided with port 156 having spouts 156a and 156b. The spout 156a is communicated with the port 154 via supplemental tube 155. The spout 156b is communicated with the second passage 40, which allows the second passage 40 to communicate with port 154 via the supplemental tube 155. First passage 38 communicates with a primary port 152.

This embodiment allows gas to be either supplied or collected from any point on the patient interface 118 and then delivered to a connector that can be assembled in any orientation. Gas may be collected or supplied at any point on the patient interface to help aid efficient venting, to supply oxygen or other gases at an effective point for nasal intake, and/or to reduce noise.

Second Embodiment Dual Cuff Connector

Figure 6:
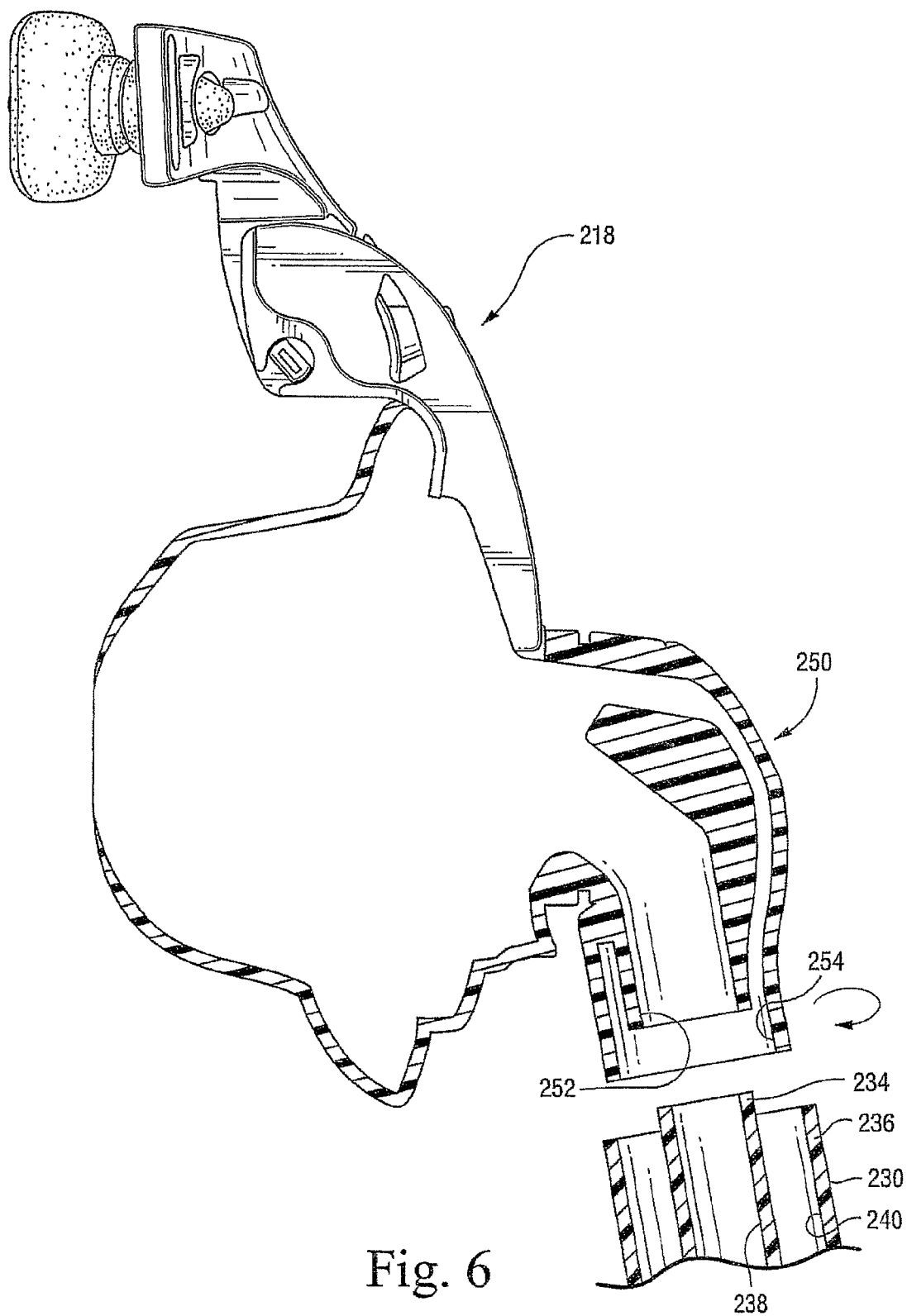
FIG. 6 is a partial cross-sectional view illustrating a connector system connected to a patient interface according to another embodiment of the present invention.

FIG. 6 illustrates a connector 230 wherein the free end of the inner tubular wall 234 is axially spaced outwardly from the free end of the outer tubular wall 236. That is, the inner tubular wall 234 protrudes outwardly from the outer tubular wall 236. FIG. 6 also illustrates a patient interface 218 wherein the secondary port 254 of the elbow assembly 250 protrudes further outwardly than the primary port 252 of the elbow assembly 250. Similar to the embodiment of FIG. 5, the connector 230 may be secured to the elbow assembly 250 with a friction fit. Specifically, the outer tubular wall 236 engages an exterior surface of the elbow assembly 250 with a friction fit, and the inner tubular wall 234 engages an interior surface of the primary port 252 with a friction fit. Additionally, the connector 230 may be rotated to any position without compromising the communication of the first and second passages 238, 240 with respective primary and secondary ports 252, 254.

Third Embodiment Dual Cuff Connector

Figure 7:
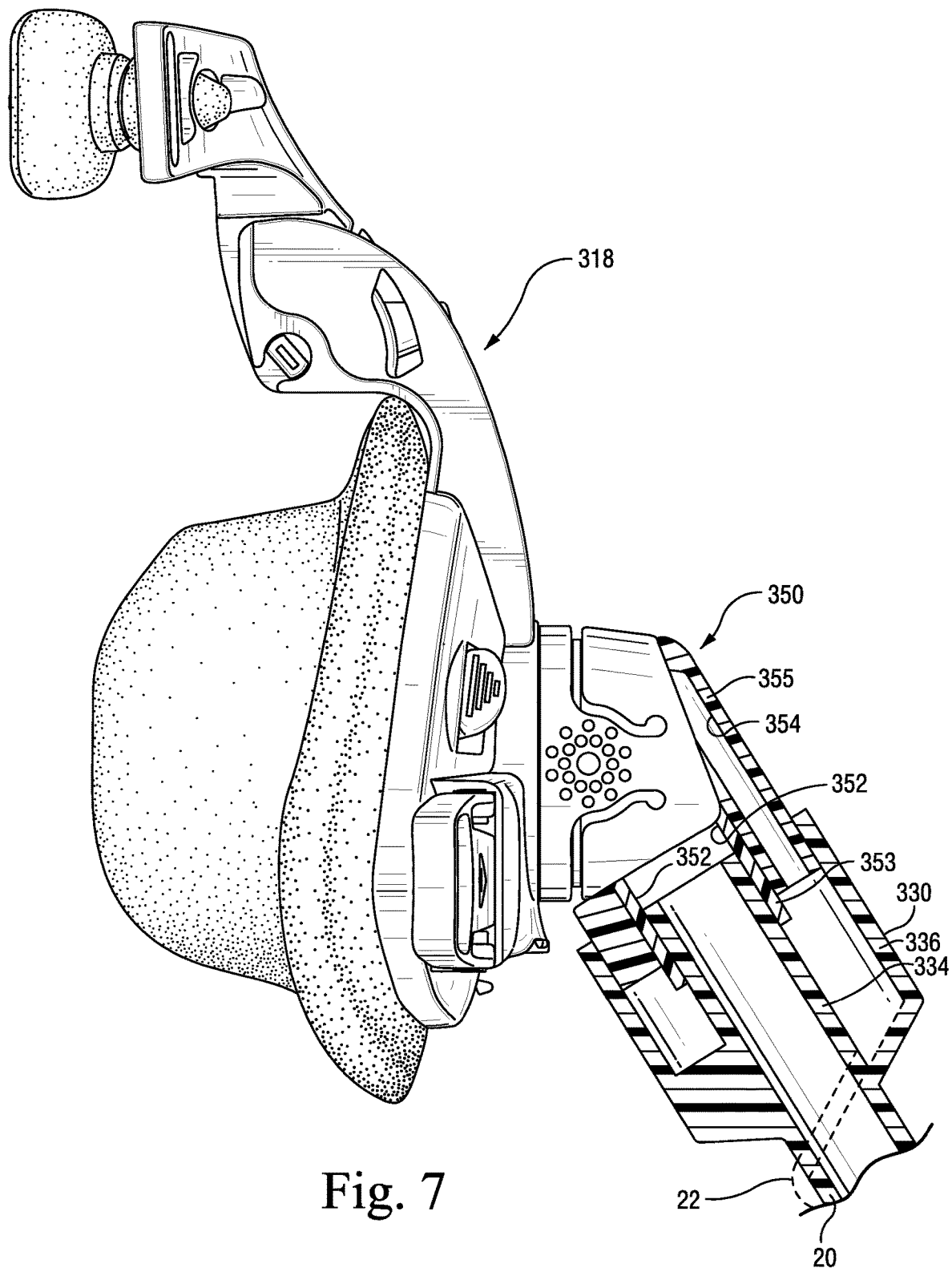
FIG. 7 is a partial cross-sectional view illustrating a connector system connected to a patient interface according to still another embodiment of the present invention.

FIG. 7 illustrates a connector 330 coupled to the elbow assembly 350 of a nasal CPAP mask assembly 318. Other than the elbow assembly, the mask assembly 318 may be structured similar to the mask assembly disclosed in ResMed's U.S. patent application Ser. No. 10/655,603, filed Sep. 5, 2003, incorporated herein by reference in its entirety. As illustrated, the elbow assembly 350 includes a primary port 352 formed in part by a conduit 353 and a secondary port 354 formed in part by a vent cover 355.

The connector 330 includes inner and outer tubular walls 334, 336 wherein the free ends are axially aligned. Similar to the embodiment of FIGS. 5 and 6, the connector 330 may be secured to the elbow assembly 350 with a friction fit. Specifically, the outer tubular wall 336 engages an exterior surface of the elbow assembly 350 with a friction fit, and the inner tubular wall 334 engages an interior surface of the primary port 352 with a friction fit. This arrangement allows the auxiliary conduit 22 to be directly communicated to the interior of the mask assembly 318, which may be beneficial for the provision of oxygen or other drug delivery, or for gas sampling or $CO_2$ removal (i.e., venting of the exhaled gas from the elbow along the auxiliary conduit 22). Additionally, the connector 330 may be coupled in any orientation, and by using different methods, e.g., snap fitting, lock fitting, or screw fit, etc.

Dual Cuff Connector Coupled to Flow Generator

Figure 8:
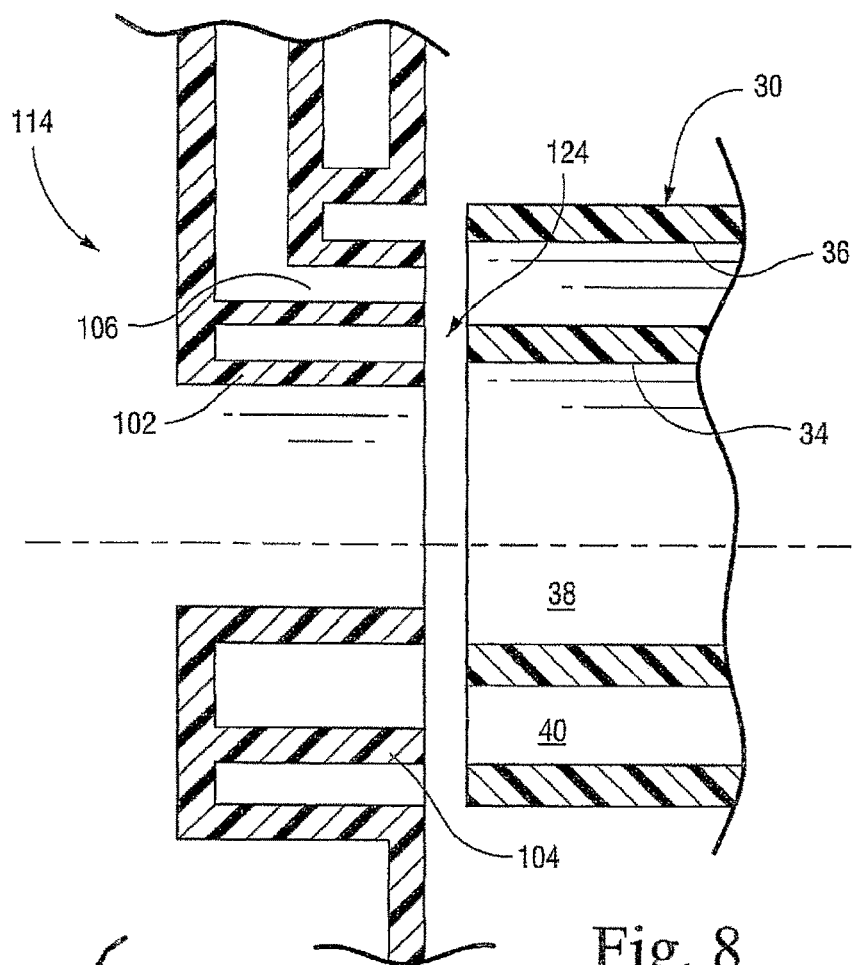
FIG. 8 is a cross-sectional view illustrating a connector system connected to a flow generator according to still another embodiment of the present invention.

FIG. 8 illustrates the connector 30 being coupled to a flow generator 114. The flow generator 114 includes an outlet 124 adapted for use with the dual cuff connector 30. Specifically, the outlet 124 includes an inner tube 102 and an outer tube 104. The inner tube 102 is communicated with a blower that provides a pressurized flow of air, and the outer tube 104 is communicated with an auxiliary conduit 106 that may be used for pressure measurement, for example. In the illustrated embodiment, the connector 30 is secured to the outlet 124 with a friction fit. Specifically, the outer tubular wall 36 engages an exterior surface of the outer tube 104 with a friction fit, and the inner tubular wall 34 engages an exterior surface of the inner tube 102 with a friction fit. However, the connector 30 may be secured to the outlet 124 in any other suitable manner. Moreover, the connector 30 may be coupled to the outlet 124 in any orientation. In use, the supply of pressurized air passes from the inner tube 102 through the first passage 38 of the connector 30, and flow from the auxiliary conduit 106 passes through the second passage 40 of the connector 30.

Coupling Arrangements of Dual Cuff Connector

The first and second passages 38, 40 of the connector 30 may be coupled or otherwise communicated with the air delivery conduit 20 and the auxiliary conduit 22 in any suitable manner. For example, the connector 30 may be integrally formed in one piece with one or both of the air delivery conduit 20 and the auxiliary conduit 22. As shown in FIGS. 2-8, the connector 30 may be integrally formed with the air delivery conduit 20 and the auxiliary conduit 22 such that the inner tubular wall 34 and first passage 38 are integral with the air delivery conduit 20 and the outer tubular wall 36 and second passage 40 are integral with the auxiliary conduit 22.

Figure 9A:
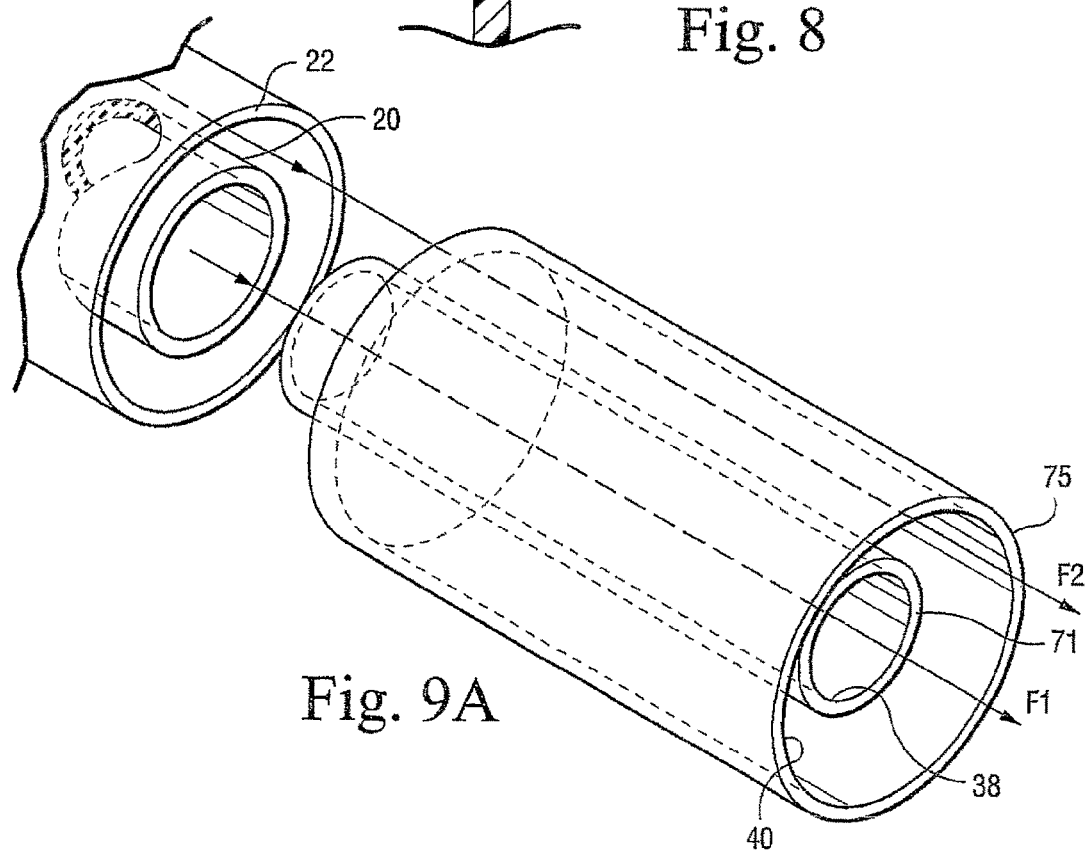
FIG. 9A is a perspective view illustrating a connector system according to still another embodiment of the present invention.

Alternatively, the connector 30 may be formed separately from the air delivery conduit 20 and the auxiliary conduit 22 and attached thereto. For example, as shown in FIG. 9A, the connector may include first and second concentric tubes 71, 75 that define the first and second passages 38, 40. Support members may be provided to support the first tube 71 within the second tube 75. In use, the first tube 71 is coupled to the air delivery conduit 20 and the second tube 75 is coupled to the auxiliary conduit 22. In the illustrated embodiment, the conduits 20, 22 have a concentric arrangement. Thus, a first flow F1 may pass through the air delivery conduit 20 and the first passage 38, and a second flow F2 may pass through the auxiliary conduit 22 and the second passage 40.

Figure 9B:
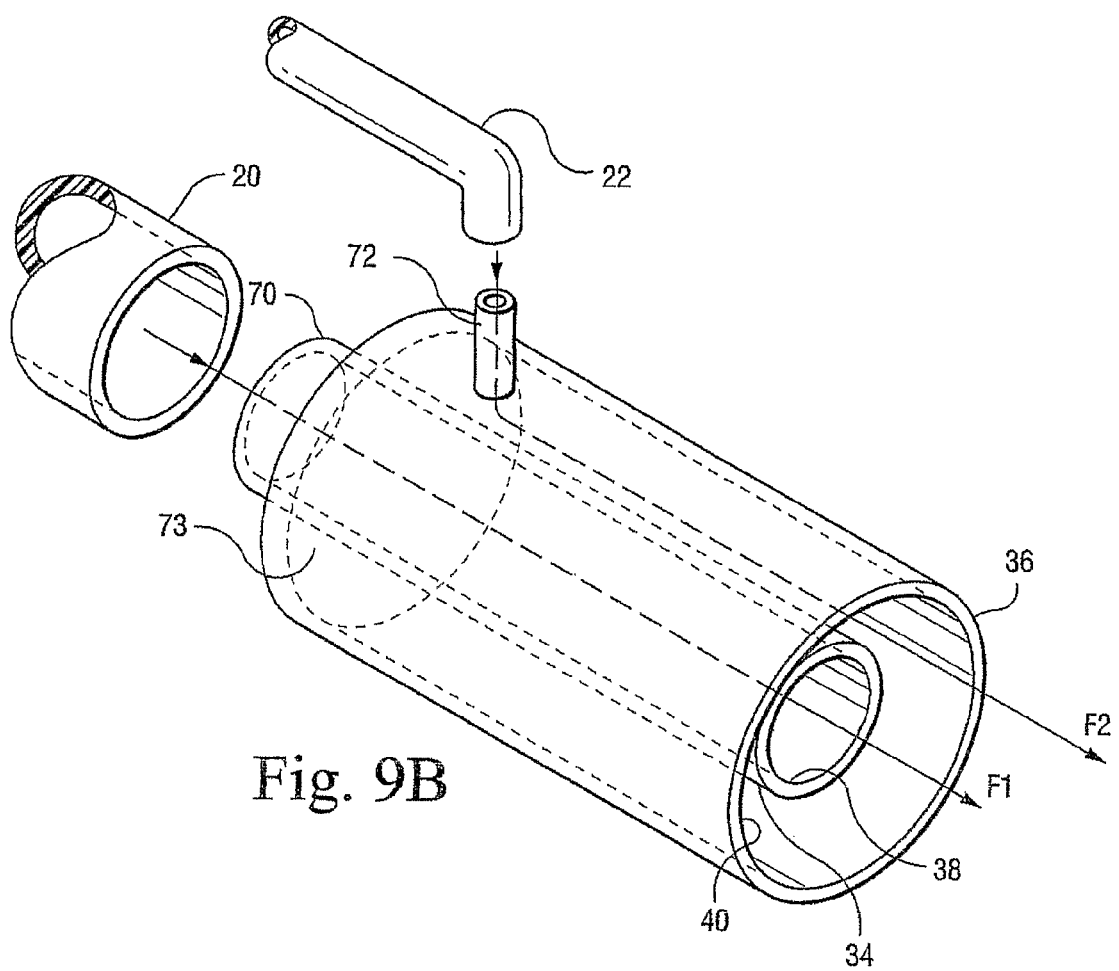
Figure 10:
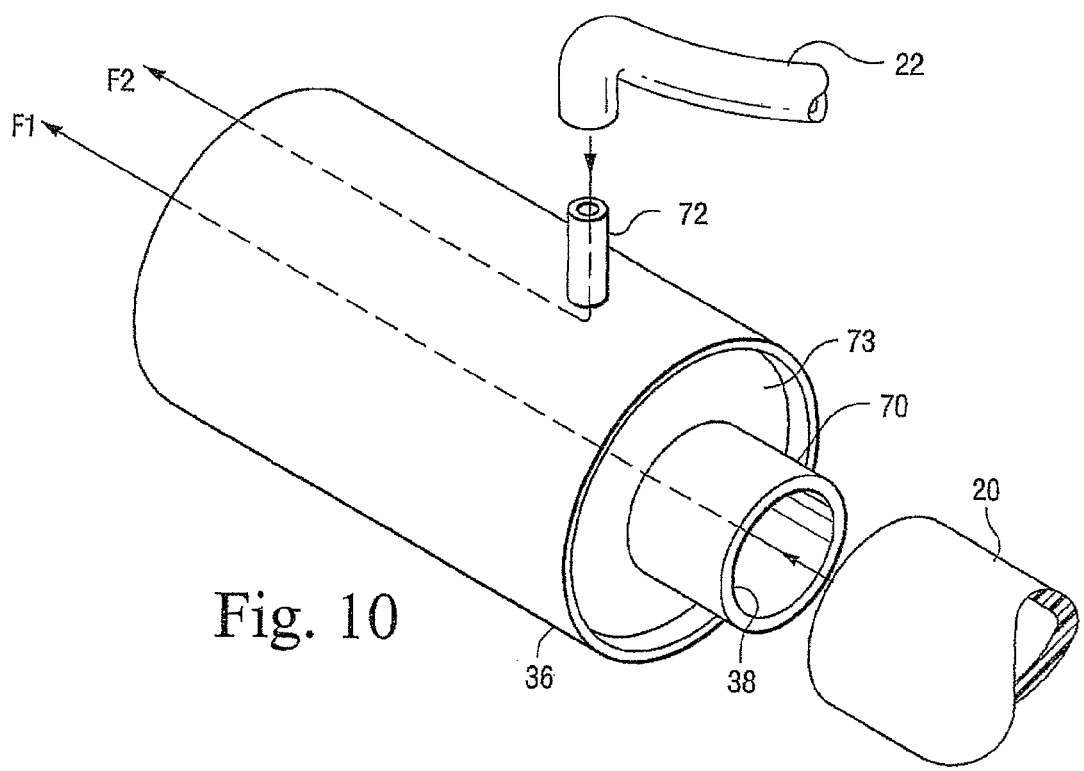

FIGS. 9B and 10 illustrates another embodiment which may be useful with an air delivery conduit where the main conduit and the auxiliary conduit are separate or loose. As illustrated, the connector 30 may include a first adapter 70, e.g., spout, communicated with the first passage 38 and a second adapter 72, e.g., spout, communicated with the second passage 40. Also, a wall 73 is provided to support the inner tubular wall 34 within the outer tubular wall 36, and to isolate the first and second passages 38, 40. In use, the first adapter 70 is coupled to the air delivery conduit 20 and the second adapter 72 is coupled to the auxiliary conduit 22. Thus, a first flow F1 may pass through the air delivery conduit 20 and the first passage 38, and a second flow F2 may pass through the auxiliary conduit 22 and the second passage 40.

Adjustment of Flow

Figure 11:
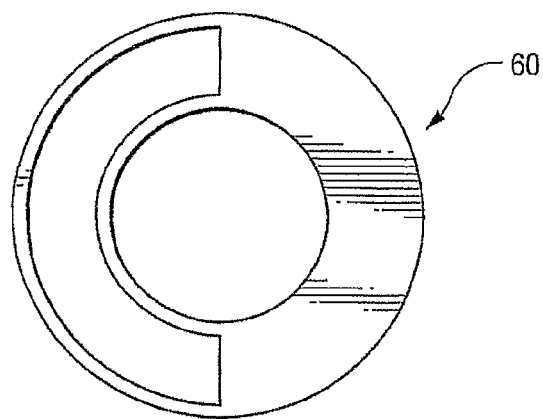
FIGS. 11-13 illustrate a connector system according to still another embodiment of the present invention.
Figure 12:
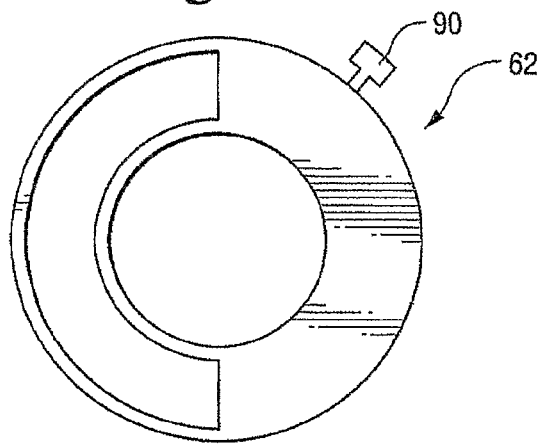
Figure 13:
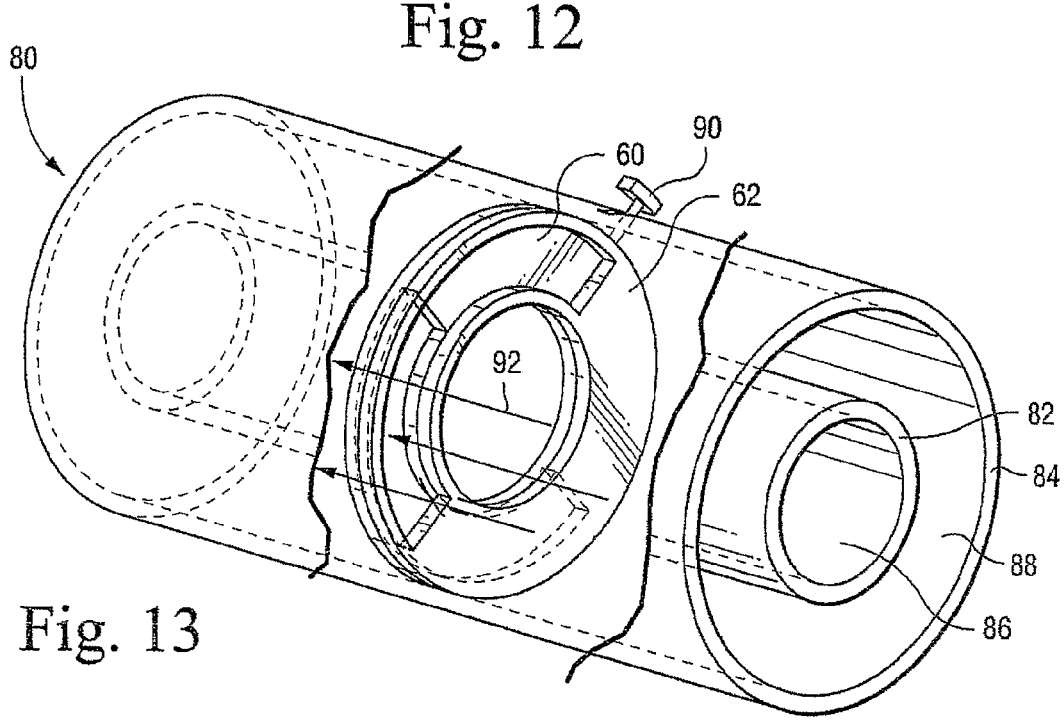

FIGS. 11-13 illustrate a flow adjustment arrangement that allows adjustment of flow through the auxiliary conduit 22. FIG. 13 illustrates an adapter 80 including first and second annular disks 60, 62 that regulate flow through the adapter 80. The adapter 80 includes first and second concentric tubes 82, 84 that define first and second passages 86, 88. The first passage 86 is communicated with the air delivery conduit 20 and the second passage 88 is communicated with the auxiliary conduit 22.

As shown in FIGS. 11 and 13, the first disk 60 is secured within the second passage 88 of the adapter 80. The first disk 60 provides structure to occlude or block off a portion, e.g., half, of the second passage 88. As shown in FIGS. 12 and 13, the second disk 62 is provided within the second passage 88, adjacent the first disk 60, and provides structure to occlude or block off a portion, e.g., half, of the second passage 88. Thus, only a portion (e.g., 0-50%) of the disks 60, 62 is open to allow flow through the second passage 88 of the adapter 80. Of course, this range can be varied according to the requirements so that a large portion of the channel (e.g., 25-75%) may be open.

Moreover, the second disk 62 includes an actuator 90, e.g., a knob that protrudes through a slot formed in the tube 84, that allows the patient to rotate the second disk 62 within the second passage 40 and with respect to the first disk 60. As shown in FIG. 13, the size of the opening or passageway (represented by arrows 92) through the disks 60, 62 may be adjusted by rotating the second disk 62 relative to the first disk 60. This arrangement allows the patient or clinician to tailor the supplemental flow provided by the auxiliary conduit 22 through the adaptor 80. However, the flow through the adapter 80 may be tailored in any other suitable manner.

Figure 13A:
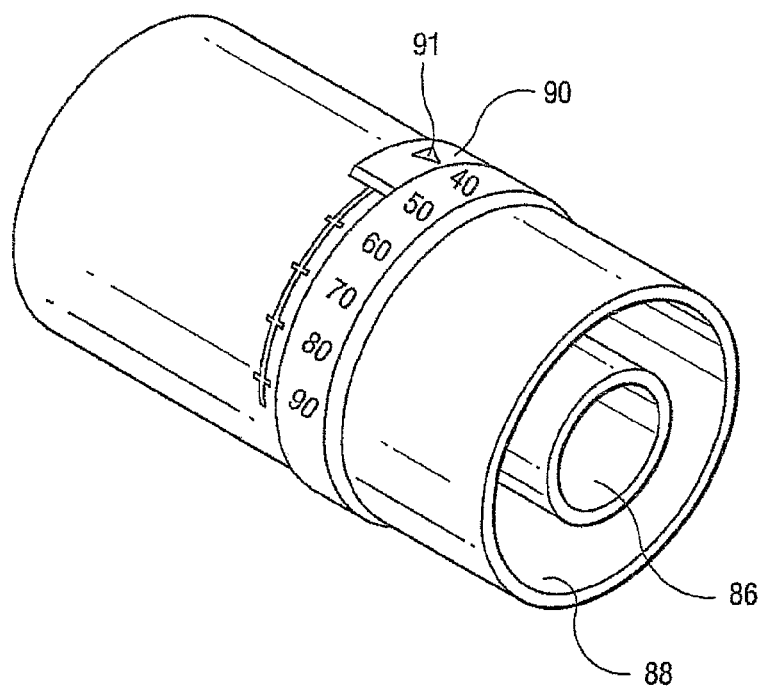
FIG. 13A illustrates an example of a flow indicator according to an embodiment of the present invention.

Also, the regulation of flow using the above-described disks may be incorporated into the connector shown in FIGS. 9A, 9B and 10, or directly into the patient interface shown in FIGS. 5-7. In an alternative embodiment, one disk may be provided in the inlet/outlet of a component (e.g., mask or blower outlet) of the apparatus 12, and another disk may be provided in the connector 30. To regulate flow, the patient or clinician may, before establishing a connection, position the connector 30 relative to the respective component so that the (fixed) disk in the connector provides the desired amount of flow through the (fixed) disk on the component. The relative positioning of the connector disk relative to the component disk will enlarge or reduce the size of the passageway through the disks. The connector and/or the component may include exterior/visible indicators that indicate the amount of flow for any given position of the connector relative to the component. For example, the arrangement shown in FIG. 13A includes a first passage 86 and a second passage 88. Second passage 88 includes a disk assembly to regulate flow therethrough. Actuator 90 includes an indicator arrow 91 that aligns with various settings, e.g., "50%", "60%", "70%", etc. to indicate how much of the second passage 88 is open.

FIG. 14 is a cross-sectional view illustrating a connector system 530 in the form of a swivel that allows unlimited 0-360° movement. Specifically, the connector system 530 includes a first connector 502 and a second connector 504 rotatably mounted to the first connector 502. Each of the first and second connectors 502, 504 includes first and second concentric tubes 582, 584 that define first and second passages 586, 588. The first tube 582 may be supported within the second tube 588 by one or more supports 592. Supports 592 still allow for the passage of air through passage 588. Moreover, each of the first and second connectors 502, 504 includes coupling elements 590, e.g., a rib and a groove, that allow the first and second connectors 502, 504 to axially interlock with one another. Preferably, at least one of the first and second connectors 502, 504 includes a circumferential groove to resiliently receive coupling elements 590, to thereby axially fix the first and second connectors 502, 504 relative to one another. When interlocked, the first and second connectors 502, 504 can swivel with respect to one another, while maintaining first and second passages 586, 588 therethrough.

Coaxial Dual Air Delivery Conduit

FIGS. 15-16 illustrate coaxial dual air conduits 621 according to embodiments of the present invention. As illustrated, each coaxial dual air conduit 621 includes an inner conduit 620, an outer conduit 622, and at least one or more support webs 625 to separate the inner and outer conduits 620, 622. In use, one of the conduits 620, 622 provides an air delivery conduit to deliver a supply of pressurized air and the other of the conduits 620, 622 provides an auxiliary conduit to vent exhaled air or provide supplemental air, pressure measurement, sound measurement, gas sampling, drug delivery, etc. The dual air conduit 621 may be coupled to a dual cuff connector 30, 230, 330 such as those described above to couple the inner and outer conduits 620, 622 to the respective component of the apparatus 12. Alternatively, the dual air conduit 621 may be directly coupled to the respective component of the apparatus 12.

In the illustrated embodiment, the inner and outer conduits 620, 622 are hoses, e.g., formed of extruded plastic, with the inner conduit 620 positioned inside the outer conduit 622. The inner and outer conduits 620, 622 are coaxial, i.e., they share the same axis. The relative diameters of the inner and outer conduits 620, 622, and their respective wall thicknesses, may be adjusted to produce the required impedances to air flow.

The inner and outer conduits 620, 622 define first and second passages 638, 640 that are isolated from one another. Specifically, the interior surface of the inner conduit 620 defines the first passage 638. The exterior surface of the inner conduit 620 and the interior surface of the outer conduit 622 define the second passage or passages 640.

The inner conduit 620 is separated from the outer conduit 622 by at least one or more support webs 625 that extend radially between the inner and outer conduits 620, 622. The support webs 625 are equally spaced about the axis of the dual air conduit 621, and preferably at least three webs 625 are provided. For example, FIG. 15 illustrates a dual air conduit 621 with four equally spaced webs 625 and FIG. 16 illustrates a dual air conduit 621 with three equally spaced webs 625. However, other suitable web arrangements are possible. The conduit 621 may be constructed of polyethylene, polypropylene, polyolefin, silicone, and the like, for example. Also, the conduits 620, 622 and webs 625 may be formed in an extrusion process for example.

The support webs 625 may be arranged in a helical fashion around the axis of the dual air conduit 621, along its length, to allow flexibility and increased crush resistance. See FIG. 15A.

The dual air conduit 621 has several advantages. For example, because the dual air conduit 621 has a coaxial arrangement, it does not require alignment with the respective component of the apparatus 12. Also, the conduit 621 has the appearance of one hose, which facilitates handling and management, thereby making the conduit 621 more comfortable and easier to use for the patient. In use; one of the conduits 620, 622 may be used for venting applications, therefore no air venting from the mask may be necessary (e.g., quieter). Further, the conduit 621 is easier to administer as the risk of cross-connection is minimized.

Low Friction Air Delivery Conduit

Figure 18:
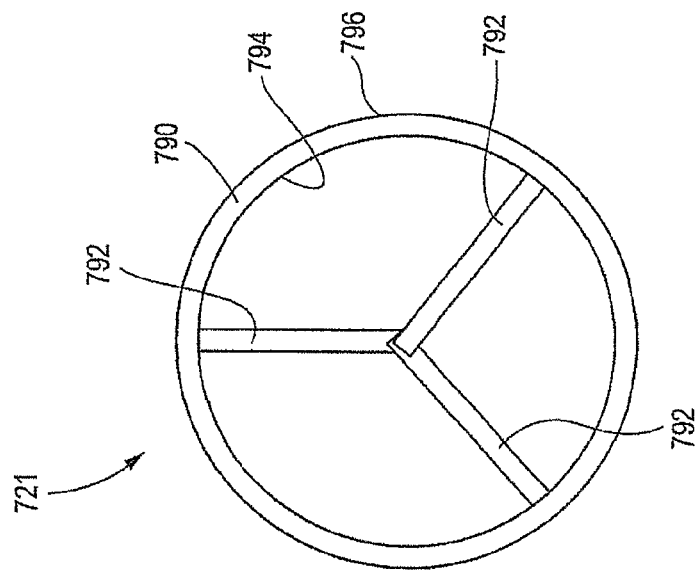
FIGS. 17-18 illustrate low friction air delivery conduits according to embodiments of the present invention.
Figure 17:
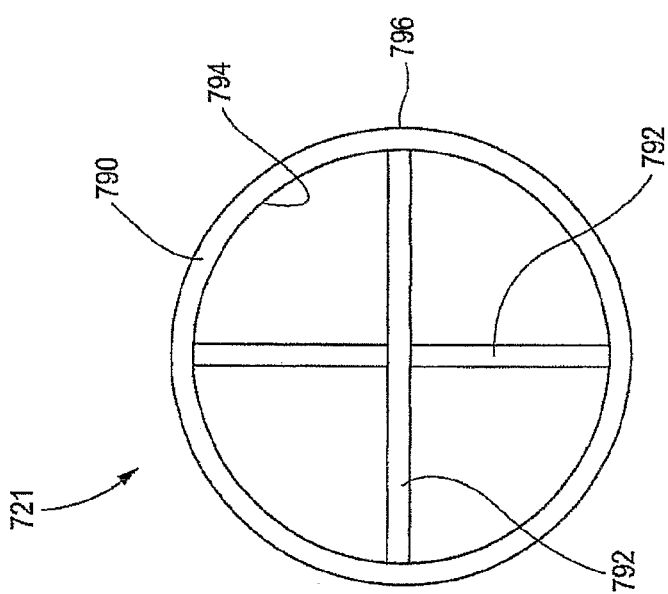
Figure 19:
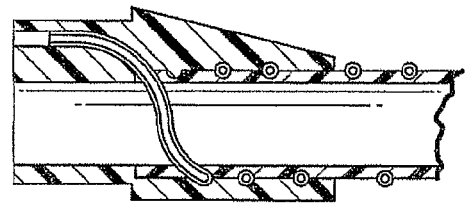
FIGS. 19-20 illustrate an embodiment of a prior art connector system (see FIGS. 5 and 6 of DE19954724).
Figure 20:
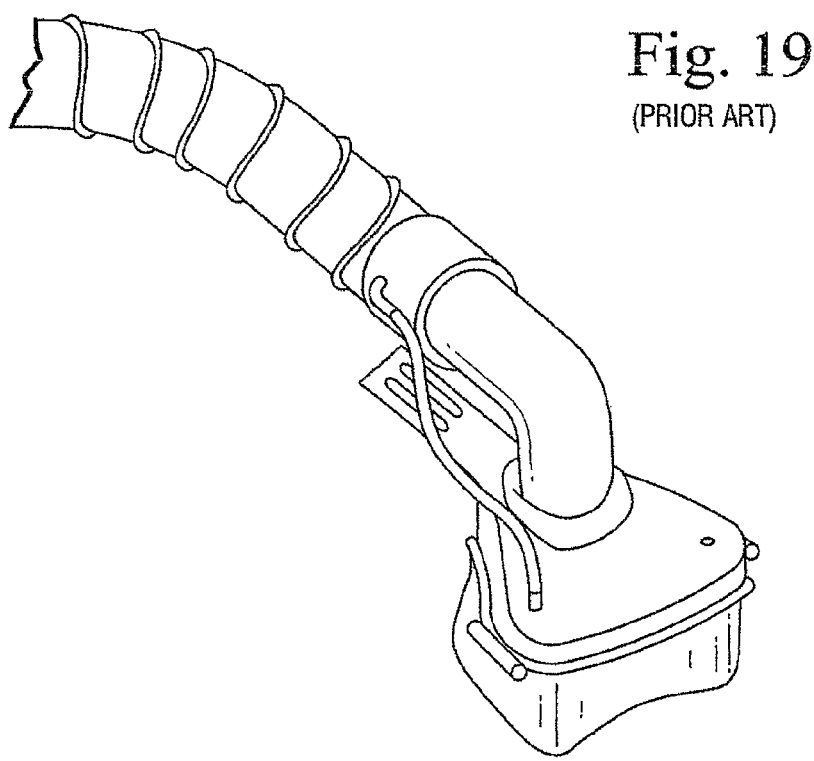

FIGS. 17-18 illustrate low friction air delivery conduits 721 according to embodiments of the present invention. As illustrated, each air delivery conduit 721 is in the form of a hose including a relatively thin tubular wall 790, e.g., formed of extruded plastic, and at least one or more support webs 792 that internally support the tubular wall 790. The conduit 721 may have any suitable length, which may depend on application.

The tubular wall 790 is structured such that both internal and external surfaces 794, 796 of the tubular wall 790 are very smooth, e.g., low friction surfaces. For example, the conduit 721 may be constructed of polyethylene, polypropylene, polyolefin, silicone, and the like. Preferably, at least the external surface 796 is smooth. The smooth external surface 796 allows the conduit 721 to slide across furniture and bed linen, for example, in a silent manner and with little resistance or friction. This provides more comfort to the patient, which may improve sleep quality and ease of use. Improved sleep quality may also lead to improved therapy.

The support webs 792 provide internal support to the tubular wall 790. As illustrated, the webs 792 extend across the internal diameter. Alternatively, the support web or webs 792 may extend across a chord of the tubular wall 790. In the illustrated embodiment, the support webs 792 are equally spaced about the axis of the tubular wall 790, and at least three webs 792 are provided. For example, FIG. 17 illustrates webs 792 arranged in a cruciform or cross shape, and FIG. 18 illustrates webs 792 arranged in tri-lobial shape wherein the webs 792 intersect at or about the axis of the tubular wall 790. However, other web arrangements are possible. The wall 790 and webs 792 may be co-extruded.

The support webs 792 may be arranged in a helical fashion around the axis of the conduit 721, along its length, to allow flexibility and increased crush resistance.

In an embodiment, the support webs 792 may define two or more isolated passages through the conduit 721. The passages may be used for air delivery, venting, electrical wiring, pressure measurement, etc.

Furthermore, there is no requirement that the conduit 721 has to be round using this system. For example, any cross-sectional shape that does not include sharp corners may be used, e.g., an oval cross-sectional shape.

Connector Advantages

An advantage of the connector 30, 230, 330 is that it does not require alignment with the respective component of the apparatus 12. The advantage arises because it is possible, in one action and without concern as to the orientation of the connector 30, 230, 330, to connect both the air delivery conduit 20 and the auxiliary conduit 22 to the respective component. This arrangement provides a less complicated assembly mechanism for the patient, thus ensuring quick assembly and preventing incorrect assembly. Additionally, the connector 30, 230, 330 is relatively small and lightweight, thereby leading to reduced drag on the patient interface and therefore less leak and a more comfortable system. The connector 30, 230, 330 is also advantageous to the physician, as it eases the incorporation of an auxiliary conduit 22, e.g., for a pressure sensor, delivery tube or gas extraction tube, into a standard air delivery conduit 20. The connector 30, 230, 330 incorporating the auxiliary conduit 22 also enables technology for more advanced systems.

Additional Embodiments

Although the illustrated embodiments only show the connector 30, 230, 330 with round tubular walls 34, 36, 234, 236, 334, 336, it should be understood that the walls may have other suitable tubular arrangements, e.g., square tube.

Although the illustrated embodiments only show the connector 30, 230, 330 being coupled to a patient interface and flow generator, it should be understood that the connector 30, 230, 330 may be coupled to other components of the apparatus 12, e.g., humidifier, in a similar manner. Also, although the illustrated embodiment illustrates an apparatus 12 that includes a humidifier 16, it should be understood that the humidifier 16 is optional and may be eliminated and the patient interface 18 may connect directly to the flow generator 14 via the air deliver conduit 20 and auxiliary conduit 22.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability to ventilators in general for use with patients and non-patients alike in medical and non-medical applications.

What is claimed is:

1. A swivel connector system comprising:
first and second air passages that are concentric with one another about a common axis;
a first connector having inner and outer walls; and
a second connector having inner and outer walls; wherein
the first air passage is at least partially defined by an inside of the inner wall of the first connector and an inside of the inner wall of the second connector;
the second air passage is at least partially defined between an outside of each of the inner walls of the first and second connectors and an inside of each of the outer walls of the first and second connectors;
the inner wall of the first connector includes a first inner coupling element adapted to interlock via a snap-fit with a second inner coupling element of the inner wall of the second connector to prevent relative axial movement but allow relative rotation, and the outer wall of the first connector includes a first outer coupling element adapted to interlock via a snap-fit with a second outer coupling element of the outer wall of the second connector to prevent relative axial movement but allow relative rotation, wherein:
a thickness of each of the inner walls of the first and second connectors is equal to a combined thickness of the first and second inner coupling elements so that the respective inner walls maintain substantially constant thickness along the axis including across a transition between the first and second connectors where the first and second inner coupling elements are interlocked; and
each of the first air passage and the second air passage comprises a substantially constant cross-section along its length so as to define a continuous and undisturbed flow along both the inside and the outside of the inner walls along the axis, including across the transition.

2. The swivel connector system according to claim 1, wherein the inner and outer walls of each of the first and second connectors include first and second concentric tubes that define the first and second concentric air passageways.

3. The swivel connector system according to claim 2, wherein the first tube is supported within the second tube by one or more supports.

4. The swivel connector system according to claim 1, wherein the first connector is interlocked with the second connector by a circumferential rib and groove arrangement.

5. The swivel connector system according to claim 4, wherein the circumferential rib and groove arrangement includes a rib and a groove, wherein in cross section, the rib includes a semi-circular projection, and the groove includes a semi-circular recess.

6. The swivel connector system according to claim 4, wherein the inner wall of the first connector includes a groove of the circumferential rib and groove arrangement and an outer wall of the first connector includes a rib of the circumferential rib and groove arrangement.

7. The swivel connector system according to claim 1, wherein the first inner coupling element of the first connector is interlocked with the second inner coupling element of the second connector by a circumferential rib and groove arrangement.

8. The swivel connector system according to claim 1, wherein the first outer coupling element of the first connector is interlocked with the second outer coupling element of the second connector by a circumferential rib and groove arrangement.

9. The swivel connector system according to claim 1, wherein the first inner coupling element of the first connector is interlocked with the second inner coupling element of the second connector by a first circumferential rib and groove arrangement, and the first outer coupling element of the first connector is interlocked with the second outer coupling element of the second connector by a second circumferential rib and groove arrangement.

10. The swivel connector system according to claim 1, wherein the inner wall of the first connector and the outer wall of the first connector have free ends that are axially aligned with one another.

11. The swivel connector system according to claim 1, wherein the outer wall of the first connector and the outer wall of the second connector have equal outside diameters.

12. The swivel connector system according to claim 1, wherein the first connector and the second connector are configured to allow 360° of relative rotation.

13. The swivel connector system according to claim 12, wherein an orientation of the outer wall of the first connector relative to the outer wall of the second connector is unchanged at any angular position.

14. The swivel connector system according to claim 1, wherein one of the first connector and the second connector is part of an elbow assembly.

15. The swivel connector system according to claim 1, wherein one of the first connector and the second connector is part of an elbow assembly of a patient interface.

16. The swivel connector system according to claim 1, wherein the inner and outer walls of each of the first and second connectors include first and second concentric tubes that define first and second concentric air passageways that are isolated from one another.

17. The swivel connector system according to claim 1, wherein the inner wall of the first connector protrudes axially outward with respect to the outer wall of the first connector.

18. The swivel connector system according to claim 1, wherein the outer wall of the first connector protrudes axially outward with respect to the inner wall of the first connector.

19. The swivel connector system according to claim 1, wherein the first and second inner coupling elements extend parallel to one another and parallel to the axis.

20. The swivel connector system according to claim 1, wherein the first and second outer coupling elements extend parallel to one another and parallel to the axis.

21. The swivel connector system according to claim 1, wherein the first inner coupling element has a diameter that is equal to and continuous with a diameter of the first air passage, the diameter of the first inner coupling element and the first air passage being equal to an inner diameter of the inner wall of the second connector.

22. The swivel connector system according to claim 21, wherein the second inner coupling element has a diameter that is equal to and continuous with an inner diameter of the second air passage, the diameter of the second inner coupling element and the inner diameter of the second air passage being equal to a diameter of an inner wall of the first connector.

23. The swivel connector system according to claim 1, wherein the first outer coupling element has a diameter that is equal to and continuous with the outer diameter of the second air passage, the diameter of the first outer coupling element and the outer diameter of the second air passage being equal to an inner diameter of the outer wall of the second connector.

24. The swivel connector system according to claim 23, wherein the second outer coupling element has a diameter that is equal to and continuous with an outer diameter of the second connector, the diameter of the second outer coupling element and the outer diameter of the second connector being equal to an outer diameter of the first connector.

25. The swivel connector system according to claim 1, wherein a thickness of the outer wall of the first connector is equal to a thickness of the outer wall of the second connector, and a combined thickness of the first and second outer coupling elements is equal to the thickness of the outer walls of the first and second connectors.

26. The swivel connector system according to claim 1, wherein the inner wall of the first connector is flush with the inner wall of the second connector, and the outer wall of the first connector is flush with the outer wall of the second connector.

27. The swivel connector system according to claim 1, wherein the first inner coupling element includes a groove to receive a rib of the second inner coupling element, and the second outer coupling element includes a groove to receive a rib of the first outer coupling element.

28. The swivel connector system according to claim 1, wherein the first outer coupling element has a surface that forms part of an outer diameter of the second air passage, and the second inner coupling element has a surface that forms part of an inner diameter of the second air passage.

29. The swivel connector system according to claim 28, wherein the first inner coupling element has a surface that forms part of a diameter of the first air passage.

30. The swivel connector system according to claim 1, wherein the first air passage is a cylinder and the second air passage is a annulus, and each of the first and second connector matches the shape of the cylinder and the annulus.

31. The swivel connector system according to claim 1, wherein the inside of the inner wall of the first connector and the inside of the inner wall of the second connector extend parallel to the axis and form a substantially continuous surface when the first inner coupling element is interlocked with the second inner coupling element.

32. The swivel connector system according to claim 1, wherein the outside of the inner wall of the first connector is disposed the same distance from the axis as the outside of the inner wall of the second connector, and wherein the inside of the inner wall of the first connector is disposed the same distance from the axis as the inside of the inner wall of the second connector.

33. The swivel connector system according to claim 1, wherein a first distance measured from the axis to the outside of the inner wall of the first connector is equal to a second distance measured from the axis to the outside of the inner wall of the second connector along the entire length of the axis, including across the transition.

34. The swivel connector system according to claim 33, wherein a third distance measured from the outside of the inner wall of the first connector to the inside of the outer wall of the first connector is equal to a fourth distance measured from the outside of the inner wall of the second connector to the inside of the outer wall of the second connector along the entire length of the axis, including across the transition.

35. The swivel connector system according to claim 1, wherein the first connector includes a first connector section and a first body section, the first connector section having the first inner coupling element and the first outer coupling element, and the inner wall and the outer wall of the first connector each having the same thickness along the entire circumference of the first body section.

36. The swivel connector system according to claim 35, wherein the second connector includes a second connector section and a second body section, the second connector section having the second inner coupling element and the second outer coupling element, and the inner wall and the outer wall of the second connector each having the same thickness along the entire circumference of the second body section.

37. The swivel connector system according to claim 36, wherein the inner wall of the first connector along the first connector section is flush with the inner wall of second connector along the second body section, thereby forming a single surface parallel to the axis.

38. The swivel connector system according to claim 37, wherein the outer wall of the second connector along the second connector section is flush with the outer wall of first connector along the first body section, thereby forming a single surface parallel to the axis.

39. The swivel connector system according to claim 38, wherein the inner wall of the second connector along the second connector section is flush with the inner wall of first connector along the first body section, thereby forming a single surface parallel to the axis.

40. The swivel connector system according to claim 39, wherein the outer wall of the first connector along the first connector section is flush with the outer wall of second connector along the second body section, thereby forming a single surface parallel to the axis.

41. The swivel connector system according to claim 1, wherein the first inner coupling element, the second inner coupling element, the first outer coupling element, and the second outer coupling element each have substantially the same thickness.

42. The swivel connector system according to claim 1, wherein the first connector and the second connector are constructed from rubber and/or plastic.

* * * * *